United States Patent
Melville et al.

[11] Patent Number: 5,982,555
[45] Date of Patent: Nov. 9, 1999

[54] VIRTUAL RETINAL DISPLAY WITH EYE TRACKING

[75] Inventors: Charles D. Melville; Richard S. Johnston, both of Issaquah, Wash.

[73] Assignee: University of Washington, Seattle, Wash.

[21] Appl. No.: 09/008,918

[22] Filed: Jan. 20, 1998

[51] Int. Cl.⁶ .............................. G02B 27/14; A61B 3/14
[52] U.S. Cl. .......................................... 359/630; 351/209
[58] Field of Search .................................. 359/629, 630, 359/631, 633; 345/7, 8; 351/206, 209, 211, 246; 382/117

[56] References Cited

U.S. PATENT DOCUMENTS

| | | | |
|---|---|---|---|
| 4,109,237 | 8/1978 | Hill | 340/146.3 |
| 4,859,846 | 8/1989 | Burrer | 250/234 |
| 4,942,766 | 7/1990 | Greenwood et al. | 73/704 |
| 5,121,138 | 6/1992 | Schermer et al. | 346/108 |
| 5,164,848 | 11/1992 | Firth et al. | 359/13 |
| 5,280,163 | 1/1994 | Barkan | 235/462 |
| 5,280,377 | 1/1994 | Chandler et al. | 359/196 |
| 5,467,104 | 11/1995 | Furness, III et al. | 345/8 |
| 5,557,444 | 9/1996 | Melville et al. | 359/199 |
| 5,568,208 | 10/1996 | Van De Velde | 351/221 |
| 5,587,836 | 12/1996 | Takahashi et al. | 359/630 |
| 5,596,339 | 1/1997 | Furness, III et al. | 345/8 |
| 5,671,076 | 9/1997 | Matsubara et al. | 359/196 |
| 5,694,237 | 12/1997 | Melville | 359/214 |
| 5,892,569 | 4/1999 | Van De Velde | 351/221 |

*Primary Examiner*—Georgia Epps
*Assistant Examiner*—Ricky Mack
*Attorney, Agent, or Firm*—Steven P. Koda

[57] ABSTRACT

Light emitted from a virtual retinal display light source passes through a beamsplitter to a scanning subsystem and on to an eyepiece and the viewer's eye. Some of the light is reflected from the viewer's eye passing back along the same path. Such light however is deflected at the beamsplitter toward a photodetector. The reflected light is detected and correlated to the display scanner's position. The content of the reflected light and the scanner position for such sample is used to generate a map of the viewer's retina. Such map includes 'landmarks' such as the viewer's optic nerve, fovea, and blood vessels. The map of the viewer's retina is stored and used for purposes of viewer identification. The viewer's fovea position is monitored to track where the viewer is looking

16 Claims, 3 Drawing Sheets

VIRTUAL RETINAL DISPLAY WITH EYE TRACKING

BACKGROUND OF THE INVENTION

This invention relates to retinal display devices, and more particularly to a method and apparatus for mapping and tracking a viewer's eye.

A retinal display device is an optical device for generating an image upon the retina of an eye. Light is emitted from a light source, collimated through a lens, then passed through a scanning device. The scanning device defines a scanning pattern for the light. The scanned light converges to focus points on an intermediate image plane. As the scanning occurs the focus point moves along the image plane (e.g., in a raster scanning pattern). The light then diverges beyond the plane. An eyepiece is positioned along the light path beyond the intermediate image plane at some desired focal length. An "exit pupil" occurs shortly beyond the eyepiece in an area where a viewer's eye pupil is to be positioned.

A viewer looks into the eyepiece to view an image. The eyepiece receives light that is being deflected along a raster pattern. Modulation of the light during the scanning cycle determines the content of the image. For a see-through virtual retinal display a user sees the real world environment around the user, plus the added image of the display projected onto the retina.

SUMMARY OF THE INVENTION

A viewer wearing a head-mounted virtual retinal display typically moves their eye as they look at images being displayed. According to the invention, the direction the viewer looks is tracked with the display. Prior to tracking, a map of the viewer's eye is generated by the display. The map includes 'landmarks' such as the viewer's optic nerve, fovea, and blood vessels. Thereafter, the relative position of one or more landmarks is used to track the viewing direction. The head-mounted display includes a light source and a scanner. The scanner deflects light received from the light source to scan a virtual image onto a viewer's retina in a periodic manner. During each scanning period, light is deflected along a prescribed pattern. To generate a map, and thereafter to monitor viewing direction, light reflected off the viewer's retina is monitored. Some of the reflected light travels back into the display device. The content of the reflected light will vary depending upon the image light projected and the features of the viewer's retina. During the initial mapping stage, the content of the image light can be fixed at a constant intensity, so that the content of the reflected light is related only to the feature's (i.e., landmarks) of the retina. The changing content of the reflected light is sampled at a sampling rate and stored. The scanner position at the time of each sample is used to correlate a position of the sample. The relative position and the content represent a map of the viewer's retina.

According to one aspect of the invention, the light reflected from the viewer's eye travels back into an eyepiece and along a light path within the retinal display device. In a specific embodiment the reflected light is deflected by the scanner toward a beamsplitter. The beamsplitter deflects the reflected light toward a photodetector which samples the reflected light content. The beamsplitter is positioned between the light source and the scanner of the retinal display device.

For generating a virtual image, light emitted from the light source passes through the beamsplitter to the scanning subsystem and onward to the eyepiece and the viewer's eye. Light reflected from the viewer's eye passes back along the same path but is deflected so as not to return to the light source. Instead the light is deflected toward the photodetector. Thus, the beamsplitter passes light which is incident in one direction (e.g., light from the light source) and deflects light which is incident in the opposite direction (e.g., reflected light from the viewer's eye).

According to another aspect of the invention, a specific feature of the retina (e.g., fovea position) is monitored over time to track where the viewer is looking (i.e., the viewer's center of vision). The landmarks in the retina which correspond to such feature will cause the reflected light to exhibit an expected pattern. The relative position of such pattern in the reflected light will vary according to the viewing direction. By identifying the pattern and correlating the relative orientation of the pattern to the orientation of the corresponding feature in the map, the change in viewing direction is determined. In various applications, such position indication is used as a pointing device or is used to determine image content. For example, as a pointing device the fovea position indicates pointer position. A blink of the eye for example, corresponds to actuating a pointing device (e.g., "clicking" a computer mouse.)

According to another aspect of the invention, the map of the viewer's retina is stored and used for purposes of viewer identification. In a security application for example, a viewer is denied access to information or denied operation of a computer or display when the viewer's retina does not correlate to a previously stored map of an authorized user.

According to an advantage of the invention, the display can track where a viewer is looking, use the viewer's eye as a pointer, and identify the person using the display. These and other aspects and advantages of the invention will be better understood by reference to the following detailed description taken in conjunction with the accompanying drawings.

DESCRIPTION OF SPECIFIC EMBODIMENTS

Overview

Figure 1:
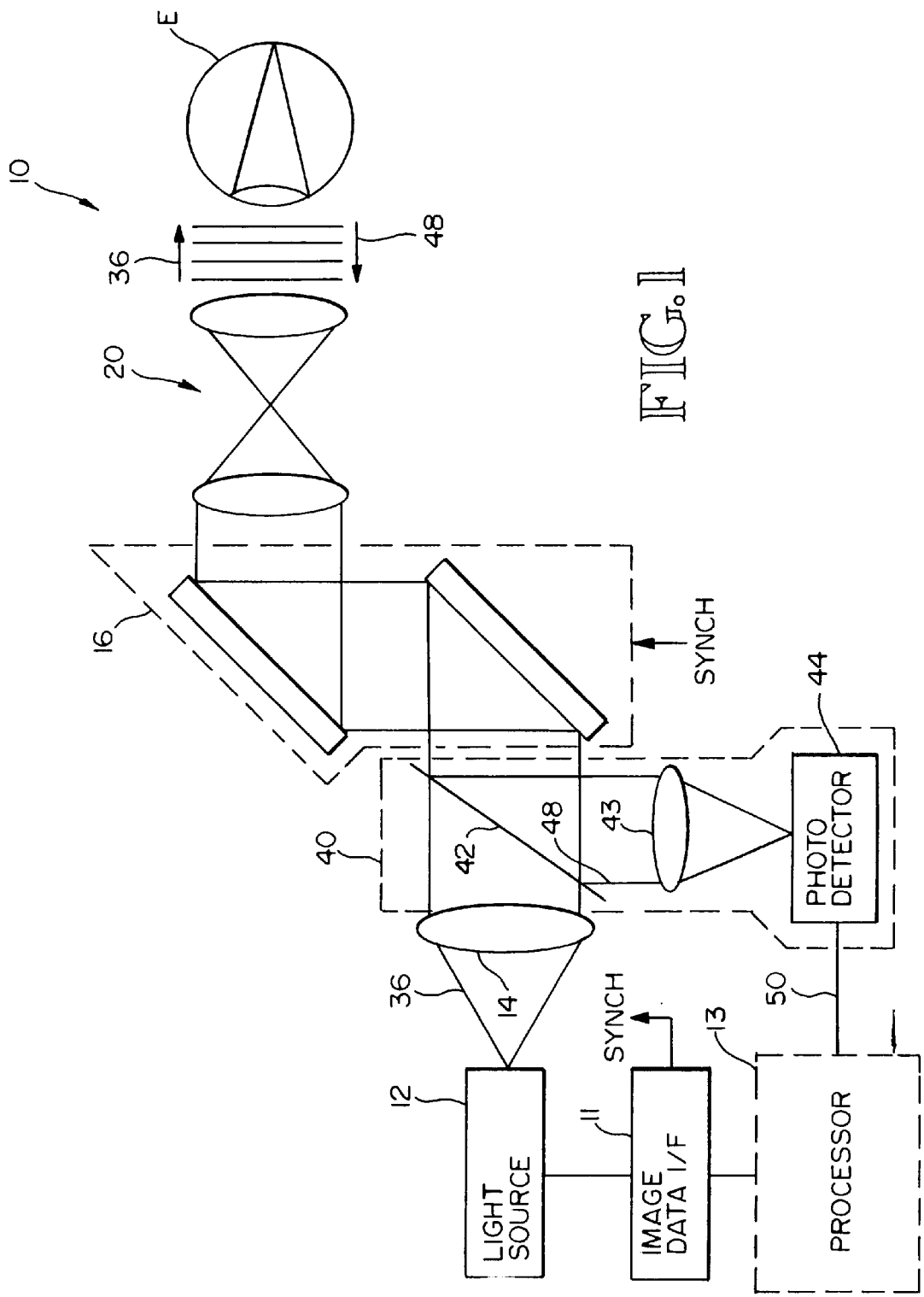
FIG. 1 is an optical schematic diagram of a virtual retinal display having an eye tracking capability according to an embodiment of this invention.
Figure 2:
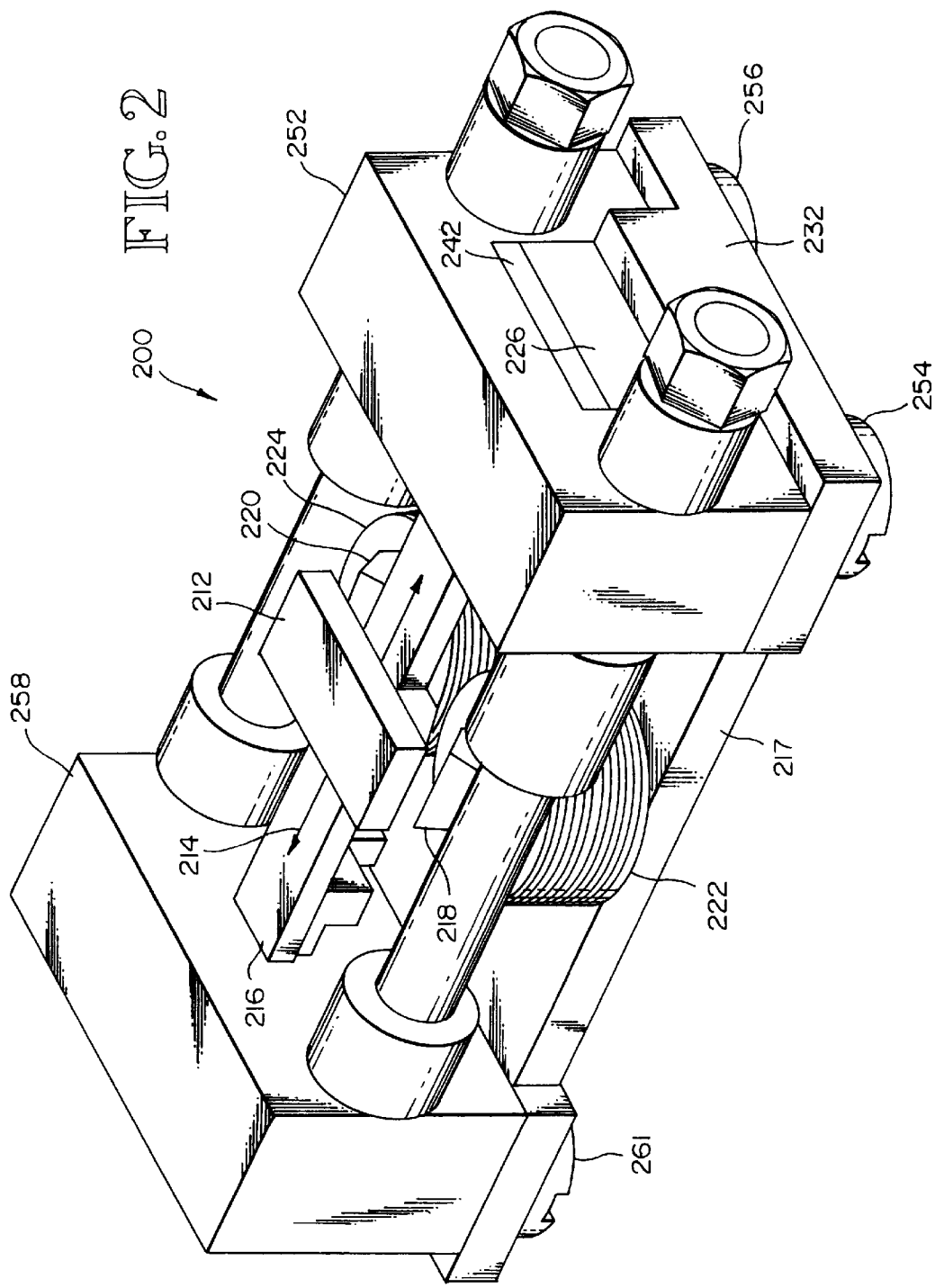
FIG. 2 is a perspective drawing of an exemplary scanning subsystem for the display of FIG. 1.

FIG. 1 is an optical schematic diagram of a virtual retinal display 10 according to an embodiment of this invention. The retinal display 10 generates and manipulates light to create color or monochrome images having narrow to panoramic fields of view and low to high resolutions. Light modulated with video information is scanned directly onto the retina of a viewer's eye E to produce the perception of an erect image. The retinal display is small in size and suitable for hand-held operation or for mounting on the viewer's head. The display 10 includes an image data interface 11 which receives image data in the form of a video or other image signal, such as an RGB signal, NTSC signal, VGA signal or other formatted color or monochrome video or image data signal. The image data is generated by a processor 13 or other digital or analog image data source. The image data interface 11 generates signals for controlling a light source 12 and for synchronizing the scanner subsystem 16. Light generated by the display 10 is altered according to the image data to generate image elements (e.g., image pixels) which form an image scanned onto the retina of a viewer's eye E. The light source 12 includes one or more point sources of light. In one embodiment red, green, and blue light sources are included. In one embodiment the light source 12 is directly modulated. That is, the light source 12 emits light with an intensity corresponding to a drive signal. In another embodiment the light source 12 outputs light with a substantially constant intensity that is modulated by a separate modulator in response to the drive signal. The light output along an optical path thus is modulated according to image data within the image signal. Such modulation defines image elements or image pixels. Preferably the emitted light is spatially coherent.

The retinal display 10 also includes a scanning subsystem 16, an eyepiece 20 and an eye mapper 40. The light 36 emitted from the light source 12 and passing through the optics subsystem 14 is deflected by the scanner subsystem 16 toward the eyepiece 20 and the viewer's eye E. In one embodiment the scanning subsystem 16 receives a horizontal deflection signal and a vertical deflection signal (e.g., SYNCH signals) derived from the image data interface 11. Typically the light is deflected along a prescribed pattern, such as a raster pattern, although in an alternative embodiment another display format such as vector imaging can be used. In one embodiment, the horizontal scanner includes a mechanical resonator for deflecting passing light, such as that described in U.S. Pat. No. 5,557,444 to Charles D. Melville entitled, "Miniature Optical Scanner for a Two Axis Scanning System," which is incorporated herein by reference. Alternatively, the horizontal scanner may be an acousto-optic device or a resonant or non-resonant micro-electromechanical device. The scanning subsystem includes a horizontal scanner and a vertical scanner. The eye mapper 40 monitors the position of the viewer's eye based upon light reflected back into the display from the viewer's eye.

Light Source

The light source 12 includes a single or multiple light emitters. For generating a monochrome image a single monochrome emitter typically is used. For color imaging, multiple light emitters are used. Exemplary light emitters include colored lasers, laser diodes or light emitting diodes (LEDs). Although LEDs typically do not output coherent light, lenses are used in one embodiment to shrink the apparent size of the LED light source and achieve flatter wave fronts. In a preferred LED embodiment a single mode monofilament optical fiber receives the LED output to define a point source which outputs light approximating coherent light.

Where the light emitters are externally modulated, the display device 10 also includes a modulator responsive to an image data signal received from the image data interface 11. The modulator modulates the visible light emitted by the light emitters to define image content for the virtual imagery scanned on a viewer's eye E. The modulator is an acoustooptic, electrooptic, or micro-electromechanical modulator.

Additional detail on these and other light source 12 embodiments are found in U.S. patent application Ser. No. 08/437,818 for "Virtual Retinal Display with Fiber Optic Point Source" filed May 9, 1995, and incorporated herein by reference.

According to alternative embodiments, the light sources or the light generated by the point sources are modulated to include red, green, and/or blue components at a given point (e.g., pixel) of a resulting image. Respective beams of the point sources are modulated to introduce color components at a given pixel.

Image Data Interface

The retinal display device 10 is an output device which receives image data to be displayed. Such image data is received as an image data signal at the image data interface 11. In various embodiments, the image data signal is a video or other image signal, such as an RGB signal, NTSC signal, VGA signal or other formatted color or monochrome video or graphics signal. An exemplary embodiment of the image data interface 11 extracts color component signals and synchronization 'SYNCH' signals from the received image data signal. In an embodiment in which an image data signal has embedded red, green and blue components, the red signal is extracted and routed to a modulator for modulating a red light point source output. Similarly, the green signal is extracted and routed to a modulator for modulating the green light point source output. Also, the blue signal is extracted and routed to a modulator for modulating the blue light point source output.

The image data signal interface 11 extracts a horizontal synchronization component and vertical synchronization component from the image data signal. In one embodiment, such signals define respective frequencies for horizontal scanner and vertical scanner drive signals routed to the scanning subsystem 16.

Scanning Subsystem

The scanning subsystem 16 is located after the light source 12, either before or after the optics subsystem 14. In one embodiment the scanning subsystem 16 includes a resonant scanner 200 for performing horizontal beam deflection and a galvanometer for performing vertical beam deflection. The scanner 200 serving as the horizontal scanner receives a drive signal having a frequency defined by the horizontal synchronization signal extracted at the image data interface 11. Similarly, the galvanometer serving as the vertical scanner receives a drive signal having a frequency defined by the vertical synchronization signal VSYNC extracted at the image data interface. Preferably, the horizontal scanner 200 has a resonant frequency corresponding to the horizontal scanning frequency.

Figure 3:
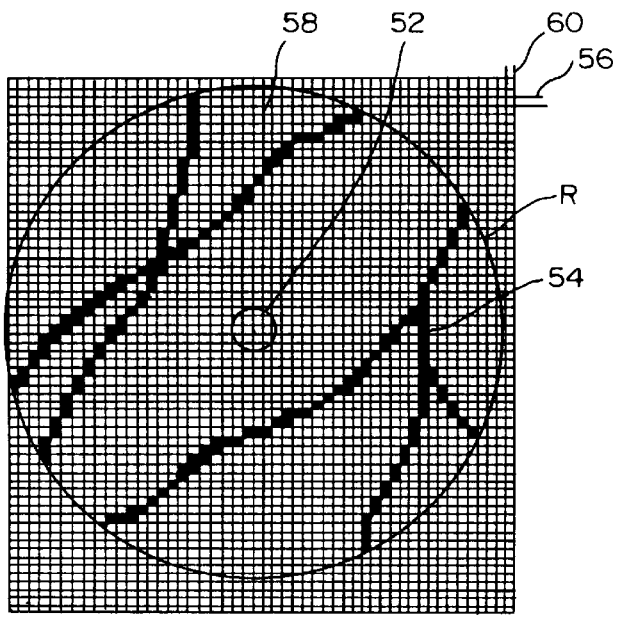
FIG. 3 is a diagram of a viewer's retina mapped according to an embodiment of this invention.

Referring to FIG. 3 the scanner 200 includes a mirror 212 driven by a magnetic circuit so as to oscillate at a high frequency about an axis of rotation 214. In one embodiment the only moving parts are the mirror 212 and a spring plate 216. The optical scanner 200 also includes a base plate 217 and a pair of electromagnetic coils 222, 224 with a pair of stator posts 218, 220. Stator coils 222 and 224 are wound in opposite directions about the respective stator posts 218 and 220. The electrical coil windings 222 and 224 may be connected in series or in parallel to a drive circuit as discussed below. Mounted on opposite ends of the base plate 217 are first and second magnets 226, the magnets 226 being equidistant from the stators 218 and 220. The base 217 is formed with a back stop 232 extending up from each end to form respective seats for the magnets 226.

The spring plate 216 is formed of spring steel and is a torsional type of spring having a spring constant determined by its length and width. Respective ends of the spring plate 216 rest on a pole of the respective magnets 226. The magnets 226 are oriented such that they have like poles adjacent the spring plate.

The mirror 212 is mounted directly over the stator posts 218 and 220 such that the axis of rotation 214 of the mirror is equidistant from the stator posts 218 and 220. The mirror 212 is mounted on or coated on a portion of the spring plate.

Magnetic circuits are formed in the optical scanner 200 so as to oscillate the mirror 212 about the axis of rotation 214 in response to an alternating drive signal. One magnetic circuit extends from the top pole of the magnets 226 to the spring plate end 242, through the spring plate 216, across a gap to the stator 218 and through the base 217 back to the magnet 226 through its bottom pole. Another magnetic circuit extends from the top pole of the other magnet 226 to the other spring plate end, through the spring plate 216, across a gap to the stator 218 and through the base 217 back to the magnet 226 through its bottom pole. Similarly, magnet circuits are set up through the stator 220.

When a periodic drive signal such as a square wave is applied to the oppositely wound coils 222 and 224, magnetic fields are created which cause the mirror 212 to oscillate back and forth about the axis of rotation 214. More particularly, when the square wave is high for example, the magnetic field set up by the magnetic circuits through the stator 218 and magnets 226 and 228 cause an end of the mirror to be attracted to the stator 218. At the same time, the magnetic field created by the magnetic circuits extending through the stator 220 and the magnets 226 cause the opposite end of the mirror 212 to be repulsed by the stator 220. Thus, the mirror is caused to rotate about the axis of rotation 214 in one direction. When the square wave goes low, the magnetic field created by the stator 218 repulses the end of the spring plate 216 whereas the stator 220 attracts the other end of the spring plate 216 so as to cause the mirror 212 to rotate about the axis 214 in the opposite direction.

In alternative embodiments, the scanning subsystem 14 instead includes acousto-optical deflectors, electro-optical deflectors, rotating polygons or galvanometers to perform the horizontal and vertical light deflection. In some embodiments, two of the same type of scanning device are used. In other embodiments different types of scanning devices are used for the horizontal scanner and the vertical scanner.

Optics Subsystem

The optics subsystem 14 receives the light output from the light source, either directly or after passing through the scanning subsystem 16. In some embodiments the optical subsystem collimates the light. In another embodiment the optics subsystem converges the light. Left undisturbed the light converges to a focal point then diverges beyond such point. As the converging light is deflected, however, the focal point is deflected. The pattern of deflection defines a pattern of focal points. Such pattern is referred to as an intermediate image plane.

Eyepiece

The eyepiece 20 typically is a multi-element lens or lens system receiving the light beam(s) prior to entering the eye E. In an alternative embodiment the eyepiece 20 is a single lens. The eyepiece 20 serves to relay the rays from the light beam(s) toward a viewer's eye. In particular the eyepiece 20 contributes to the location where an exit pupil of the retinal display 10 forms. The eyepiece 20 defines an exit pupil at a known distance from the eyepiece 20. Such location is the expected location for a viewer's eye E.

In one embodiment the eyepiece 20 is an occluding element which does not transmit light from outside the display device 10. In an alternative embodiment, an eyepiece lens system 20 is transmissive so as to allow a viewer to view the real world in addition to the virtual image. In yet another embodiment the eyepiece is variably transmissive to maintain contrast between the real world ambient lighting and the virtual image lighting. For example a photosensor detects ambient lighting. A bias voltage is generated which applies a voltage across a photochromatic material to change the transmissiveness of the eyepiece 20.

Eye Mapper

The eye mapper 40 is positioned between the light source 12 and the scanning subsystem 16. In an embodiment where the optics subsystem is located between the light source 12 and the scanning subsystem 16, the eye mapper 40 is positioned between the optics subsystem 14 and the scanning subsystem 16. The eye mapper 40 includes a beamsplitter 42, a convergent lens 43, and a photodetector 44. The photodetector 44 generates an electronic signal which is input to the processor 13. In one embodiment the processor 13 is part of a computer which generates the image data for the display 10. The beamsplitter 42 passes light 36 which is incident in one direction and deflects light 48 which is incident in the opposite direction. Specifically, the beamsplitter 42 passes light 36 received from the light source 12 and deflects light 48 reflected back from the viewer's eye E through the scanning subsystem 16.

To form an image on the viewer's retina light 36 emitted from the light source 12 passes through the optics subsystem 14, through the beamsplitter 42, into the scanning subsystem 16 and on to the eyepiece 20 and the viewer's eye E. Some of the photons of light are absorbed by the eye's retina. A percentage of the photons, however, are reflected back from the retina. The reflected light 48 travels back through the eyepiece 20 and is deflected by the scanning subsystem 16 back to the beamsplitter 42. The beamsplitter 42 deflects the reflected light 48 toward the photodetector 44. The photodetector 44 samples the reflected light content generating an electronic signal 50.

Mapping a Viewer's Retina

According to one method of this invention, the retinal display 10 with eye mapper 40 is used to map a viewer's eye. FIG. 3 shows a diagram of an exemplary retina R of a viewer, as mapped according to an embodiment of this invention. The human retina includes a fovea 52 and several blood vessels 54 which are poor reflectors of light. Other parts of the retina R are better reflectors of light. Of the photons reflected back from the retina R, there is relatively less reflection at the fovea 52 and the blood vessels 54 than at other portions of the retina.

To generate an image on the viewer's retina R, the image is scanned in a raster or other prescribed pattern. For example, a light beam is modulated as the beam moves horizontally across an eye. Multiple horizontal rows 56 are scanned onto the eye to complete the raster pattern. The timing for modulating the light beam is synchronized so that the row consists of multiple pixels 58 of light. Thus the raster pattern includes multiple rows 56 and columns 60. When the light is forming a pixel at a given location on the retina R, such location also may reflect a portion of the impinging photons back into the display 10. Such photons form light 48 reflected back through the eyepiece 20 and scanning subsystem 16 to the beamsplitter 42. The photons are then deflected to the photodetector 44. A given sample of reflected light 48 comes from a given part of the retina and correlates such part of the retina to the relative position of the scanner within its raster pattern at the time such reflected light is detected. Along the course of a raster scan of the image onto the eye, there is a pattern of light reflected back to the eye. While generating a map of the retina, the light source 12 typically does not modulate the light. As a result, any changes in light incident on the photodetector 44 is due to a change in reflectance at a portion of the retina. Alternatively, the light striking the retina may be modulated and synchronously detected for greater noise immunity. In another alternative, modulated image light may be used to map the retina. Variations in intensity or content are filtered out by conventional comparison techniques for common mode rejection. A sample of the electronic signal generated by the photodetector 44 is taken for each pixel scanned onto the eye. For each pixel, the reflected light is registered as a high or a low logic state. One logic state corresponds to reflected light being above a threshold intensity. The other logic state corresponds to the reflected light being below the threshold intensity. The samples compiled for an eye are a map of such eye's retina R. The resulting map is stored for use in various applications. Using conventional image processing techniques, the pattern of logic states are analyzed to define the fovea 52 and one or more blood vessels 54. Preferably, when compiling a map of a viewer's retina, the viewer is instructed to look straight ahead at an unchanging image. Alternatively, where the scanning subsystem is sufficiently fast, the mapping may occur during real time—meaning the eye mapper 40 can map the eye features simultaneously with virtual image generation.

Tracking a Viewer's Eye Position

Figure 4:
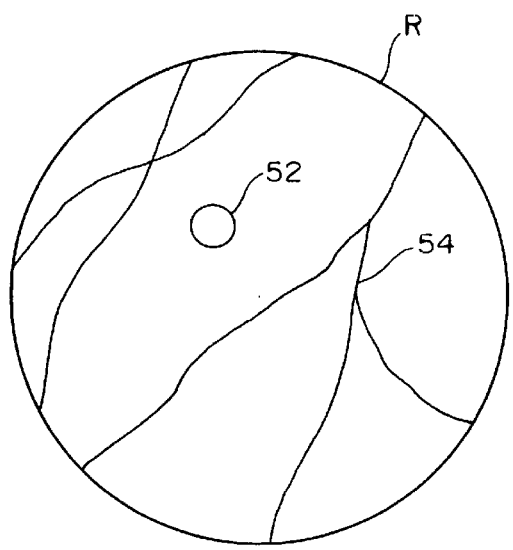
FIG. 4 is a diagram of the viewer's retina of FIG. 3 at a time when the viewer looks in a different direction.

One application of the eye mapper 40 is to track a viewer's eye position. According to one embodiment of this invention, the location of the viewer's fovea within a map at a given point in time is taken as the direction in which the viewer is looking. For example, FIG. 3 shows the fovea 52 at the center of the retina R. This corresponds to the viewer looking straight ahead. FIG. 4 shows a view of the same retina R with the viewer looking in a different direction. In FIG. 4 the fovea 52 is to the left of center and upward of center. From the viewer's perspective, the viewer is looking right of center and upward. The amount the fovea has moved left of center and upward of center determines the degree that the viewer is looking right of center and upward, respectively. Precise angles can be achieved for the viewing angle based upon the location of the fovea 52.

Rather than monitoring relative change in orientation of the fovea, in an alternative method the location of the fovea within the current scanning pattern is identified. The processor uses the position of the fovea to identify a group of pixels that the viewer is focusing on. The identification of the group of pixels determines a viewing orientation within the current field of view. Alternatively, the viewing orientation could be correlated to an external environment, such as the airspace around aircraft. The correlated location or orientation in the external environment may be used for image capture (e.g., photography), weapons targeting, navigation, collision avoidance, human response monitoring, or a variety of other applications.

Method for Identifying Viewer

An application for using a stored map of a viewer's eye is to identify the viewer. For example, only authorized viewer's having maps of their retina previously stored on a computer system may be allowed access to the computer system of to select information on the computer system or computer network. In a preliminary mode, a map of a user is obtained and stored. A set of access privileges then are identified and programmed into the computer system for such user. When such user desires to access the computer system, the user's retina is scanned. Such scanning results in a second map of the viewer's retina R. Such second map is compared to the previously stored map. If the two maps correlate within to a threshold percentage, then the user is identified as being the user for such stored map. Preferably, the user is instructed to look at the same angle as when the initial map was obtained and stored. However, the precise viewing angle may not be achievable by the viewer. However, by comparing the relative location between the fovea 52 and various blood vessels 54, the two maps are correlated. Thus, even for a different viewing angle the pattern of blood vessels and the fovea will be the same, just skewed. Depending on the degree of difference in the viewing angle, the skew may or may not be linear. The skew is nonlinear because the retina is not flat. As the retina moves the angle changes the apparent skewing. However, using conventional correlation techniques it can be determined, for example, that the retina of FIGS. 3 and 4 are the same. The viewer is just looking at a different direction for the two figures.

Method for Pointing Within an Image

Figure 5:
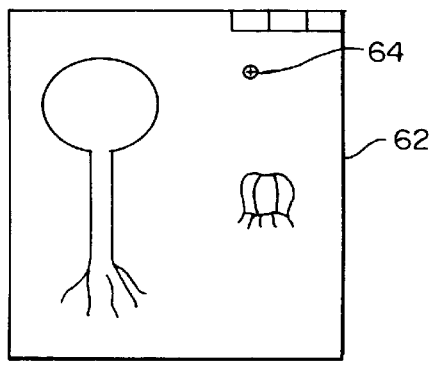
FIG. 5 is a diagram of a display image.

As described above, the position of the fovea 52 is used to identify the viewing angle. The position of the fovea 52 is tracked over time as the viewer moves their eye. At any given instant, such viewing angle defines where within the virtual image the viewer is looking. Specifically, the viewing angle correlates to a specific location on the virtual image. According to an embodiment of this invention, such specific location is used to define a pointer for the viewer. For example, in one embodiment a cross hair is overlaid onto the virtual image at the location where the viewer is looking. In another embodiment a cursor is overlaid. FIG. 5 shows an exemplary virtual image 62 with an overlaid cross-hair 64. Such cross-hair is overlaid onto the virtual image within 1–2 frames of the image, (e.g., frames are updated at approximately 60 Hz; faster refresh rates also are known for displaying image data). Such 1–2 frame latency is a substantial improvement of prior eye tracking devices. The latency is low according to this invention, because the position of the reflected light returning from the eye is immediately correlated to the particular pixel within the raster pattern. The overhead for identifying and updating the fovea position and for altering the location of the cross hair in the output image is minimal and is done within a frame period (i.e., resulting in a 1–2 frame latency).

Figure 6:
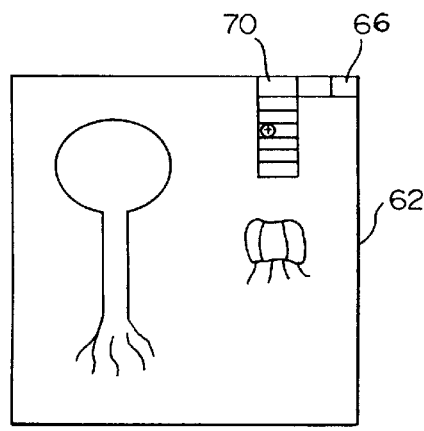
FIG. 6 is a diagram of a display image after a viewer clicks on a button on the display imagery.

According to another aspect of this invention the viewer's eye not only functions as a pointing device (e.g., a mouse) but also functions as a clicking device (e.g., a mouse button). In one embodiment two blinks correspond to a click of a mouse. Alternatively one blink can be used or more blinks can be used. Use of at least two blinks, however, is less likely to result in inadvertent clicking due to inadvertent blinking by a user. FIG. 6 shows an example where a viewer points to a menu line 66 along the top of a virtual image 62. By blinking or double blinking at a given menu within the menu line 66, the menu opens. FIG. 6 shows a menu 70 pulled down. The viewer then can select an item within the menu 70. As shown, the viewer is looking at the third item in the menu 70.

Figure 7:
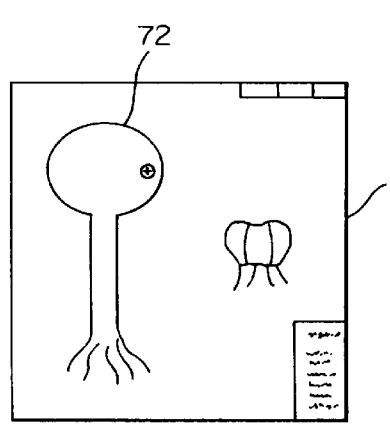
FIG. 7 is a diagram of a display image after a viewer clicks on a target among the display imagery.

FIG. 7 shows another application of the pointing and clicking functions. The viewer is looking at a target image 72 within the virtual image 62. By blinking or double blinking on such target image 72, text or graphic information relating to such target appears on the image 62. Such information is applied at a prescribed location. In the illustrated example, information of the target image 72 appears in the lower right hand corner of the image 62. Because the computer system generates the virtual image and knows the content of the virtual image and knows where the viewer is looking when the viewer blinks, the computer can determine at what portion of the virtual image 62 the viewer is looking. Information about such portion, if any, then is overlaid onto the image 62.

Although a preferred embodiment of the invention has been illustrated and described, various alternatives, modifications and equivalents may be used. For example, although the embodiment described herein maps the user's retina, the display may alternatively map other features of the eye, such as iris characteristics or capillary structures. Therefore, the foregoing description should not be taken as limiting the scope of the inventions which are defined by the appended claims.

What is claimed is:

1. A method for generating a map of a viewer's retina with a virtual retinal display, the method comprising the steps of:

generating light;

receiving the generated light at an input of a lensing system, the lensing system defining a first optical path from the input toward an output, the lensing system output adapted for transmitting light to the and receiving light from a viewer's eye, the lensing system including a beam deflector and a beam splitter located along the optical path;

receiving light reflected from the viewer's eye;

deflecting the generated light along a raster pattern with the beam deflector;

concurrently deflecting the reflected light received from the viewer's eye with the beam deflector;

redirecting with a beamsplitter the deflected reflected light along an alternative optical path;

detecting the redirected light with an optical detector responsive to the redirected light to produce an electrical signal corresponding to the redirected light.

2. A display appartus, comprising:

an image source for generating light;

a lensing system having an input aligned to the image source for receiving the generated light, the lensing system having an output adapted for transmitting light to and receiving light from a viewer's eye, the lensing system defining an optical path from the input to the output;

a beamsplitter in the optical path which redirects light received from the viewer's eye along an alternative optical path;

an optical detector positioned in the alternative optical path and responsive to the redirected light to produce an electrical signal corresponding to the redirected light;

a memory device storing data representing a reference level; and a processor coupled to the detector and to the memory device, the processor being responsive to the electrical signal and the data to produce a signal indicative of a relationship between the electrical signal and the reference level.

3. A display apparatus comprising:

an image source for generating modulated light based upon a sequence of modulated values;

a lensing system having an input aligned to the image source for receiving the generated modulated light, the lensing system having an output adapted for transmitting modulated light to and receiving corresponding reflected light from a viewer's eye, the lensing system defining an optical path from the input to the output;

a beamsplitter in the optical path which redirects light received from the viewer's eye along an alternative optical path;

an optical detector positioned in the alternative optical path and responsive to the redirected light to produce an electrical signal corresponding to the redirected light; and a processor coupled to the detector, the processor being responsive to the electrical signal and the sequence of modulated values to determine a viewing orientation of the viewer's eye.

4. The display apparatus of claim 3, in which over time the processor produces a first group of indicative signals which are stored in the memory device and correspond to a map of the viewer's eye.

5. The display apparatus of claim 4, in which the map is a first map, and wherein over time the processor produces a second group of indicative signals which correspond to a second map of the viewer's eye, the processor comparing the second map to the first map to determine whether the first map and second map correspond to a common eye.

6. The display apparatus of claim 3, in which the processor comprises means for positioning a display object within the virtual image as a function of the viewer's eye position.

7. A display apparatus, comprising:

an image source for generating light;

a lensing system having an input aligned to the image source for receiving the generated light, the lensing system having an output adapted for transmitting light to and receiving light from a viewer's eye, the lensing system defining an optical path from the input to the output;

a beamsplitter in the optical path which redirects light received from the viewer's eye along an alternative optical path;

an optial detector positioned in the alternative optical path and responsive to the redirected light to produce an electrical signal corresponding to the redirected light; and a scanner along the optical path, the scanner deflecting the generated light along a raster pattern, the scanner concurrently deflecting the light received from the viewer's eye.

8. A virtual retinal display apparatus with eye tracking, the apparatus receiving an image data signal for generating a virtual image upon a viewer's eye, the apparatus comprising:

an image light source which modulates image light as a function of the image data signal to output modulated image light which defines the virtual image in a sequence of display pixels;

a scanner receiving the modulated visible light, the scanner deflecting the received visible light along a raster pattern, the scanner receiving a synchronization signal correlating to timing of a portion of the raster pattern;

a photodetector;

wherein the scanner receives returning light reflected from the viewer's eye, the scanner deflecting the returning light;

a beamsplitter receiving the deflected returning light from the scanner, the beamsplitter directing said deflected returning light toward the photodetector, the photodetector generating a first signal in response to detection of the returning light; and a processor receiving the first signal and the synchronization signal, for correlating samples of the first signal to a timing position within the synchronization signal.

9. The apparatus of claim 8, in which the processor comprises means for generating a map of the viewer's eye based upon the first signal and the synchronization signal.

10. The apparatus of claim 9, in which the processor comprises means for storing the map as a first map, and means for comparing a second map to the first map to determine whether the first map and second map correspond to a same eye.

11. The apparatus of claim 8, in which the processor comprises means for identifying a viewer's eye position over time based upon the first signal and the synchronization signal.

12. The apparatus of claim 11, in which the processor comprises means for positioning a display object within the virtual image as a function of the viewer's eye position.

13. A method for generating a map of a viewer's retina with a virtual retinal display, the method comprising the steps of:

receiving an image data signal at the display to define image content of an image to be scanned upon a viewer's retina;

generating light modulated as a function of the image data signal;

deflecting the light along a raster pattern with a light scanner;

receiving returning light reflected from the viewer's eye at the light scanner, deflecting the returning light toward a beamsplitter;

directing said deflected returning light with the beamsplitter toward an optical detector;

generating a first signal at the optical detector in response to detection of the returning light; and correlating respective samples of the first signal to corresponding timing positions within the raster pattern, wherein the correlated samples define the map of the viewer's retina.

14. The method of claim 13, further comprising the steps of:

storing the map as a first map; and comparing a second map to the first map to determine whether the first map and second map correspond to a same eye.

15. The method of claim 13, further comprising the step of identifying a viewer's eye position over time based upon relative location of a select data pattern within the first signal, wherein the select data pattern corresponds to a fovea of the viewer's eye.

16. The method of claim 13, further comprising the step of positioning a display object within the virtual image as a function of the viewer's eye position.

* * * * *